United States Patent
Bond et al.

(10) Patent No.: US 8,283,182 B2
(45) Date of Patent: Oct. 9, 2012

(54) AGGLUTINATION BASED SAMPLE TESTING DEVICE

(75) Inventors: Damian Joseph Peter Bond, Bacup (GB); Stephen John Minter, New Mills (GB); Timothy John Minter, Brighton (GB)

(73) Assignee: Platform Diagnostics Limited, Ossett (GB)

( * ) Notice: Subject to any disclaimer, the term of this patent is extended or adjusted under 35 U.S.C. 154(b) by 0 days.

(21) Appl. No.: 12/813,896

(22) Filed: Jun. 11, 2010

(65) Prior Publication Data

US 2011/0136257 A1     Jun. 9, 2011

Related U.S. Application Data

(63) Continuation of application No. 10/549,966, filed as application No. PCT/GB2004/001199 on Mar. 18, 2004, now abandoned.

(30) Foreign Application Priority Data

Mar. 18, 2003   (GB) .................................. 0306098.5

(51) Int. Cl.
*G01N 21/75*   (2006.01)
*G01N 33/566*   (2006.01)
(52) U.S. Cl. ........................................ 436/501; 422/412
(58) Field of Classification Search .................. 422/412; 436/501
See application file for complete search history.

(56) References Cited

U.S. PATENT DOCUMENTS

| | | |
|---|---|---|
| 3,951,606 A | 4/1976 | Moyer et al. |
| 4,756,884 A | 7/1988 | Hillman et al. |
| 4,963,498 A | 10/1990 | Hillman et al. |
| 5,486,335 A | 1/1996 | Wilding et al. |
| 5,628,961 A * | 5/1997 | Davis et al. ..................... 422/63 |
| 5,837,546 A | 11/1998 | Allen et al. |
| 6,235,241 B1 | 5/2001 | Catt et al. |
| 6,764,581 B1 | 7/2004 | Forrow et al. |
| 2001/0034068 A1 * | 10/2001 | Spivey et al. ................. 436/518 |
| 2002/0187071 A1 | 12/2002 | Law |

(Continued)

FOREIGN PATENT DOCUMENTS

EP   0057110 A2   8/1982

(Continued)

*Primary Examiner* — Lore Jarrett
(74) *Attorney, Agent, or Firm* — Janet Sleath; Speckman Law Group PLLC (57) ABSTRACT

A sample testing device for testing for the presence of a component of interest in a liquid sample comprises: (a) at least one capillary pathway which has an upstream end and a downstream end and which incorporates a reagent system capable of causing agglutination with said component to be detected (the test capillary); (b) preferably, but optionally, at least one capillary pathway having an upstream end and a downstream end (the control capillary); (c) a sampling region to which the liquid sample is applied and from which the sample is able to enter the upstream ends of the test capillary (s) and if present the control capillary(s); (d) a power source; (c) detection arrangements electrically associated with said power source for detecting the presence of liquid at a downstream region of said testing capillary(s) and if present the control capillary(s); (f) display means operated by said power source for indicating the result of the test; and (g) signal processing means associated with the power source, detection arrangement and display means for evaluating the result of the test and providing said result on the display means. The device may be used for a pregnancy test, more particularly for determining the presence of hCG in urine.

20 Claims, 2 Drawing Sheets

U.S. PATENT DOCUMENTS

| | | | | |
|---|---|---|---|---|
| 2004/0238358 | A1* | 12/2004 | Forrow et al. | 204/403.01 |
| 2006/0263907 | A1* | 11/2006 | Zweig | 436/524 |

FOREIGN PATENT DOCUMENTS

| | | | |
|---|---|---|---|
| EP | 0212314 | A2 | 3/1987 |
| EP | 0321736 | A2 | 6/1989 |
| EP | 0483117 | A2 | 4/1992 |
| EP | 0485368 | A2 | 5/1992 |
| EP | 0999786 | B1 | 11/2002 |
| WO | 9009596 | A1 | 8/1990 |
| WO | 93/22054 | A1 | 11/1993 |
| WO | 9322054 | A1 | 11/1993 |
| WO | 93/24231 | A1 | 12/1993 |
| WO | 95/13531 | A1 | 5/1995 |
| WO | 96/05510 | A2 | 2/1996 |
| WO | 97/46868 | A1 | 12/1997 |
| WO | 98/43739 | A2 | 10/1998 |
| WO | 99/35497 | A2 | 7/1999 |
| WO | 0033063 | A1 | 6/2000 |
| WO | WO0033063 | * | 6/2000 |
| WO | 2004/083859 | A1 | 9/2004 |

* cited by examiner

FIG. 3

AGGLUTINATION BASED SAMPLE TESTING DEVICE

REFERENCE TO RELATED APPLICATIONS

This application is a continuation of U.S. patent application Ser. No. 10/549,966, filed Sep. 16, 2005, which is the US national phase entry of PCT patent application no. PCT/GB04/001199, filed Mar. 18, 2004, which claims priority to UK patent application no. GB 0306098.5, filed Mar. 18, 2003.

TECHNICAL FIELD

The present invention relates to a sample testing device for testing for the presence of a component of interest (i.e. an analyte) in a liquid sample. The invention relates particularly, but by no means exclusively, to such a device for use in the home, doctor's surgery or clinic by unskilled users to allow for self-diagnosis of certain conditions, for example pregnancy.

BACKGROUND

Hand held devices for the detection of analytes in a sample of, for example, urine, are known. The use of such devices as home tests for pregnancy and fertility is now commonplace and a wide variety of test devices and kits are available commercially. Many of these devices rely on capillary action. Thus, the use of strip material (e.g. a membrane) along which a liquid sample will travel by capillary action in devices for the detection of analytes by specific binding assays, such as immunoassays, has previously been proposed. Generally, a liquid sample is applied to the strip material and permeates throughout the strip material to a region impregnated with a specific binding partner for the analyte under test. The analyte bound to the specific binding partner migrates further along the strip where it is immobilized at an indicator region impregnated with an immobilizing agent specific for the analyte bound specific binding partner. The extent to which the analyte present in the sample becomes immobilized at the indicator region is determined by labelled reagents either incorporated in the strip or applied subsequently thereto. Generally, the presence of immobilized analyte at the indicator region provides a color change at the indicator region and it is the detection of that color change by the user that indicates the presence of the particular analyte in the sample. Such devices are widely used as home pregnancy and fertility tests.

A problem associated with known analyte assay devices is that there is scope for error associated with the reading of the color change. Generally the specific binding partner for the analyte is labelled with a visible colored label, for example latex particles impregnated with a dye. The indicator region of the test strip in a known device generally would contain an amount of an immobilizing agent which stops the analyte within the indicator zone so that the amount of label at the indicator zone builds up to give a visible color change. The presence of this immobilizing agent may provide a slight amount of color to the indicator region and it is this color that is intensified when a positive result is observed. For example, the strip at the indicator region may be pale blue. When the test has been used and the analyte has bound a labelled antibody, which is immobilized at the indictor region, the strip at the indicator region may be a darker blue. The color change is not easily reproducible or accurately readable by eye, especially under varying light conditions.

Furthermore, in tests which require reading a color change by eye, a user of an analyte assay device may have a preferred outcome to the assay in mind when reading the assay results and this may cloud their interpretation of the color change. For example, a user of a pregnancy test kit (such as based on an antigen/antibody binding reaction for the detection of hCG) which indicates pregnancy by an intensification of the color at the indicator region may see an intensification in color more readily if they wanted to be pregnant than if they did not want to be pregnant. This leads to error in determining the presence of the analyte and the condition which is associated with the presence of that analyte, in this case pregnancy.

Another factor can arise from the test continuing to run after the initial result is given. The test is optimized to give a result in a short time frame, 1-3 minutes. However the antibody-antigen binding reaction continues to occur as long as the test strip is wet and analyte can flow. Since every sample of female urine will contain a basal level of hCG, it is possible that over time sufficient color can build up to be detectable.

In order to overcome the above disadvantages, electrochemical detection has been proposed for pregnancy testing devices. Thus, for example, PCT publication WO-A-00 00827 discloses a device in which a specific binding partner for the analyte has a label which is directly or indirectly electrochemically detectable, the device further comprising an electrochemical detection arrangement. The electrochemically detectable label may, for example, be a P1 nuclease label, in which case the carrier of the device also incorporates all of the substrates and enzymes, other than P1 nuclease, necessary to generate hydrogen peroxide in a reaction catalyzed by P1 nuclease. The electrochemical detection arrangement serves to detect the presence (or otherwise) of hydrogen peroxide. The device of WO-A-00 00827 may incorporate a LED or LCD display device for illustrating the result of the test.

A further proposal using an electrochemical detection arrangement is disclosed in WO-A-0033063. The device of this WO specification comprises a substrate along which a liquid may travel by capillary action. Provided on the substrate is at least one pair of electrodes of dissimilar metal arranged such that liquid flowing along the substrate comes between the electrodes and causes a current to be generated for operating an electrochemical detection arrangement of the device. Once again, the result of the test may be displayed, for example, on a LCD display device.

A further assay device incorporating electronic, visually readable output means (e.g. an LCD) is disclosed in WO-A-9506240 (Metrika Laboratories, Inc.). This WO specification discloses a disposable self-contained, electronic assay device for use in determining the amount of one or more analytes in a body fluid such as blood or urine. The device comprises a card-like housing having a receiving region to which liquid sample is applied and a sample, treatment region to which the sample passes. The sample treatment region is capable of producing a physical detectable change if the analyte is present in the sample (or present above a predetermined amount). The change may, for example, be a color change. The device further comprises a detector, signal processing means and an electronic display device together with a power source for operating these three components. Any change at the sample treatment area (caused by the analyte) is sensed by the detector so that the signal processing means is able to determine the result of the test and provide a readout on the display device.

By way of further background to the present invention, reference is also made to WO-A-99 35497 (Bio-Diagnostics Limited) which discloses a device for testing liquids. The device specifically disclosed in WO-A-99 35497 is for identifying blood groups and comprises a co-operating plate and lid arrangement which together define a number of capillary channels, each having an upstream end into which blood to be tested is introduced and a downstream vent (to allow blood flow along the capillaries). The device incorporates three capillary channels which, part way along their lengths, are formed into one or other of the 'indicator letters' A, B or 0 (i.e. blood group designations). Upstream of the indicator letters, each capillary channel has an agglutination reagent system that will cause agglutination of blood which is of a type represented by the indicator letter of that channel. Thus, for example, the channel formed with 'A' as the 'indicator letter' incorporates an agglutination reagent system that will cause agglutination of blood type A (but not types B or 0). There is a further capillary track (along which blood may travel) which does not include an agglutination system and which has a 'check mark' instead of an 'indicator letter'. Apart from the 'indicator letters' and the 'check mark' (all of which are initially colorless) the device otherwise has a red background.

To determine blood group type, a blood sample is introduced at the upstream ends of the capillary tracks. Blood should flow unhindered along the track associated with the 'check mark' which will then become colored red as an indication that the device is functioning properly. This track can therefore be considered as a 'control track'.

Depending on the blood type of the sample under test, the blood will become agglutinated in one of the other three tracks but will flow along the other two. Thus, for example, if the blood group is of the type A then the blood will become agglutinated in the track having the 'A' as the 'indicator letter'. Blood in this track is therefore not able to reach the 'indicator letter'. In contrast, blood is able to flow fully along the other two tracks and fill the 'indicator letters' associated therewith. Thus after the test has been conducted two of the 'indicator letters' as well as the 'check mark' will have become colored red and will no longer be visible against the red background of the device. The remaining 'indicator letter' in the pathway in which blood has been agglutinated will however still remain clear and thus the blood type is determined.

SUMMARY

According to the present invention there is provided a sample testing device for testing for the presence of a component of interest in a liquid sample, the device comprising:
(a) at least one capillary pathway which has an upstream end and a downstream end and which incorporates a reagent system capable of causing agglutination with said component to be detected (the test capillary);
(b) preferably, but optionally, at least one further capillary pathway having an upstream end and a downstream end (the control capillary)
(c) a sampling region to which the liquid sample is applied and from which the sample is able to enter the upstream ends of the test capillary(s) and if present the control capillary(s);
(d) a power source;
(e) detection arrangements electrically associated with said power source for detecting the presence of liquid at a downstream region of said testing capillary(s) and if present the control capillary(s);
(f) display means operated by said power source for indicating the result of the test; and
(g) signal processing means associated with the power source, detection arrangement and display means for evaluating the result of the test and providing said result on the display means.

The device of the invention, which is preferably constructed as a hand-held device, is useful for the rapid analysis of samples (generally a liquid sample) to detect the presence (or otherwise) therein of a component of interest (also referred to herein as the analyte) and provide, on the display means, a read-out of the test result. As described more fully below, a particular embodiment of the invention is a pregnancy testing device which is capable of analysis for the presence (or otherwise) in urine of a hormone (e.g. human Chorionic Gonadotropin) which is associated with pregnancy. The invention is not however limited to pregnancy testing devices and many other analysis formats are possible.

Devices in accordance with the invention may be constructed as single use devices which may be employed for carrying out a single assay and then disposed of.

The or each capillary pathway is preferably in the form of a capillary tube. It is however also possible for the capillary pathways to be formed in a chromatographic or other membrane, e.g. of nitrocellulose. Further possibility is for the or each capillary pathway to be formed of porous or fiber material (e.g. the pathway is formed in a hollow fiber).

The device of the invention incorporates one or more capillary pathways each of which is associated with a detection arrangement for detecting the presence (or otherwise) of liquid at a downstream region of the respective pathway. One of these pathways, i.e. that designated as (a) above, is a 'testing' pathway and the other, i.e. that designated as (b) above (if present) is a 'control' pathway'. The control pathway if present is such that liquid introduced into the upstream end thereof is capable of flowing, under capillary action, at least as far as the detection arrangement associated with that pathway. This provides a signal to the signal processing means confirming that liquid has travelled to the required extent along the control pathway. This, in effect, confirms that the device is functioning normally. The 'testing pathway' is also such that liquid sample introduced into its upstream end is (at least initially) capable of flowing by capillary action along the 'testing pathway'. However the testing pathway incorporates a reagent system which is capable of causing agglutination with the analyte either (depending on the intended sensitivity of the device) if the analyte is present or present in an amount above a predetermined value. If the appropriate condition is met then the agglutination will either stop the flow along the testing pathway so that liquid does not reach the associated detection arrangement or will cause the flow to be slowed down such that liquid does not reach the detection arrangement by a predetermined time interval in which the test procedure is to be completed.

In use of the device, the liquid sample to be tested is applied to the sampling region from which it enters the upstream ends of both pathways. The sampling region may for example include an absorbent pad to which the liquid sample is applied and from which it enters the capillary pathways. Alternatively, the sampling region may be a reservoir, with a one-way valve, designed so that liquid can enter from the outside, but cannot exit by the same route. Alternatively, the sample can be applied using a pipette or similar application device.

The question as to whether or not the liquid sample introduced into the upstream end of the testing pathway is able to reach the detection arrangement associated with that pathway (or reach that arrangement within a predetermined time) depends on whether or not agglutination has occurred along that pathway (i.e. on whether or not the sample under test contains the analyte or at least in an amount above a predetermined value). The result of the test is determined by the signal processing means based on the inputs it has received from the detection arrangements associated with the capillary pathways. In the example of the single test pathway if the liquid has reached the detection arrangement, before a specified time, then the result of the test will be determined as 'negative' (i.e. the analyte is not present in the sample or is not present above a predetermined amount, as appropriate) and an appropriate message can be shown on the display device. In the example of a device incorporating both testing and control pathways, if the liquid has reached the detection arrangement associated with both the control and testing pathways then the result of the test will be determined as 'negative' (i.e. the analyte is not present in the sample or is not present above a predetermined amount, as appropriate) and an appropriate message can be shown on the display device. Alternatively if liquid has not reached the detection arrangement associated with the testing pathway within a specified time or at all, then the result of the test is 'positive' and once again an appropriate message is displayed (if liquid did not reach the detection arrangement associated with the control pathway then a message such as Test Void would be displayed).

The agglutination system will be selected depending on the component to be detected in the sample. The agglutination system may however comprise a binding partner (for example, in certain cases, an antibody) for the component. The agglutination system most preferably comprises particles (e.g. latex beads having a size of 300 µm to 10 um, depending upon the size and concentration of the target analyte—in the case of hCG particle sizes of 1-10 um are preferred) on which the binding partners are immobilized. Alternatively or additionally binding partners may be immobilized on the walls of the capillary.

For agglutination to occur each molecule of analyte must be capable of binding two or more particles. In the case where the analyte is hCG, the particles may be provided with binding partners specific for the two chains on the hCG molecule (i.e. one against the alpha chain and one against the beta chain. The purpose of a dual epitope system is spatially to separate the binding events so that they are in different parts of the analyte molecule. This gives greater reliability of forming an agglutination complex in low analyte numbers.

The agglutination system utilizes two physical principles to slow the flow rate and block the capillary pathway. In the optimal design, the agglutination reaction occurs rapidly and a plug is formed, which creates a dam, blocking flow of liquid. Alternatively, the agglutination complexes form a drag on the flow of the liquid and act as a counter force to the forward draw of capillary pressure. When the draw equals the forward force, the liquid front runs out of energy and flow stops. The choice of mechanism will depend upon the kinetics of the binding reaction and the speed of forming the agglutination complex, although in practice a combination of both effects can be anticipated. The development of the agglutination system is assisted by depositing the particle-binding partner complex in the early part of the test track. In the embodiments mentioned below in which the test track has four 180° bends (presenting five parallel sections), the particle-binding partner complex will be laid in the first and second sections, allowing agglutination to build up as the liquid passes through them.

Another approach is to form a dam, which impedes liquid flow, but is soluble in a defined time in an aqueous environment, to allow the agglutination complex to maximize, before flow could occur. A physical barrier constructed of approximately 25% carboxymethyl cellulose offers the correct time delay.

The formation of the agglutination complex can be further enhanced by inclusion of constructs to form the backbone of a three dimensional lattice. One example would be poly-lysine chains, with specific binding partners attached, so that hundreds of particles could be bound to one rigid structure.

Alternatively, for assays that require blockage for a low number of small target analytes, pre-agglutinated complexes can be laid down in the pathways, such that they are capable of free flowing, but in the presence of a low number of binding events, form sufficient aggregations to block or slow the flow.

Where it is important to localize the agglutination event, the binding partner can be bound onto the surface of the capillary pathway, either as individual molecules, or as complexes, such as the poly-lysines structure with the binding partners attached. This will encourage or force the localized binding of the particle-binding partner-analyte complex in a precise location. The optimal position is likely to be at the beginning of the final lane of the capillary pathway, so that there has been time for the agglutination reaction to build into the largest complex before reaching the localized binding site.

The agglutination reagent system will generally be specific for the analyte to be determined. A wide range of agglutination reagent systems are however known to those skilled in the art and individual sampling devices may readily be constructed for a correspondingly wide range of analytes. A device in accordance with the invention may for example be constructed for detecting a specific peptide hormone in a liquid sample. Alternatively a device may be constructed for determining a particular bacteria or virus as the analyte. For all of these possibilities, the agglutination reagent system may comprise an antibody (or antibodies) for the analyte. It is possible, for example, for the device to include a reagent system comprising two different 'types' of antibody, one of which recognizes a first epitope on the analyte and the other of which recognizes a second epitope. A portion of the antibodies may be immobilized on latex beads and the remainder may be immobilized on the inner walls of the capillary of the test pathway.

In order to enhance sensitivity of the device (e.g. to enhance the change in flow rate) it is possible for the test capillary to incorporate a particulate material that will effectively change the dimensions of the capillary. Examples of such particulate materials are inert materials such as silica and bentonite. Alternatively the particulate material may be a swellable polymer such as Sephadex G100 or G50. The particulate material may be admixed with the agglutination reagent system or laid down separately in the test capillary, generally downstream of the agglutination reagent system.

It should be appreciated that the control pathway (if present) may incorporate the same material as the test pathway, except the "agent" that effects agglutination. Thus for example if the agglutination reagent system comprises latex beads with antibody bound thereto then the control pathway may also incorporate latex beads but without antibody. Similarly any particulate material as described above (e.g. silica, bentonite or Sephadex) that is present in the test pathway may also be present in the control pathway, ideally in a similar way (e.g. admixed with latex beads).

Thus, devices in accordance with the invention may be constructed for a wide range of liquid samples, e.g. of biological or environmental origin.

A particularly preferred construct of device in accordance with the invention is a pregnancy testing device which analyses for the presence of hCG in urine. In such a device, the agglutination reagent system will comprise anti-hCG antibody.

The length of the capillary pathways between their inlet ends and the detection arrangement will typically be in the range of 50-350 mm. The precise length will be determined by a number of factors, including, size of analyte, number of analyte molecules and speed required to read result. The pathways may be linear but to reduce the overall length of the device can turn through angles part way along their length. One form of the device envisages 180° angles so that a 350 mm capillary pathway has four 180° bends, presenting 5 lanes in a width of 6 mm and a length of 70 mm.

The testing pathway may incorporate partial obstructions along its length, e.g. weirs as disclosed in WO-A-9935497. Such obstructions can further assist in slowing flow rate, or blockage by a combination of forming a partial dam and by altering the force of the capillary action in the pathway.

Conveniently the capillary pathways are formed by a co-operating plate and lid. Open-topped passage ways may be formed in the plate and the lid then applied so as to form the actual capillary pathway. The plate (with its open-top channels) may be produced by a moulding operation which can form the partial obstructions for the channels. Additionally the agglutination system may be incorporated into the channel forming the test pathway before the lid is applied. The plate and lid may be formed of a hydrophilic plastic or a hydrophobic plastic which has been associated with hydrophilic elements to enhance capillary action. A surface treatment of the hydrophilic plastic is one option. Alternatively use of a hydrophilic lid is a preferred solution.

The device incorporates signal processing means that are operatively linked to the display device and the liquid detection arrangements associated with the capillary pathway(s). These detection means may for example comprise pairs of electrodes, each such pair being within (or being associated with) each or any of the capillary pathways at or towards the downstream end thereof. For the purposes of detecting liquid, a potential difference is applied across the electrodes of each pair. Liquid that has reached any one pair of electrodes will allow a current to flow across that pair of electrodes and this will be detected by the signal processing means for the purposes of evaluating the result of the test.

A detection arrangement comprised of such electrodes is particularly suitable where the liquid is conductive per se if the liquid is not conductive then (solid) electrolyte may be deposited in the capillary pathway(s) upstream of the detection electrodes so that (with the dissolved electrolyte) the liquid has become conductive by the time it reaches the electrodes.

Alternatively the detector may be an optical detector. For example, the detector may comprise a reflectometer. For the purposes of optical detection, a dye or dyed particles may be laid down in the capillary pathway(s) upstream of the detector. Liquid passing through the portion of the pathway(s) having the dye or dyed particles becomes colored for the purpose of optical detection.

The signal processing means may incorporate a timer that is activated at the start of the test. In this case, the test is conducted for a predetermined period of time to determine whether or not the liquid reaches the detection arrangements associated with the testing pathway within that time. This caters for the possibility that, for a 'positive' test, the agglutination reagent system does not completely stop liquid flow but prevents it reaching the detection arrangement (associated with the testing pathway within a predetermined time). Alternatively the timing may be activated at a point part way along the track, e.g. half way along the capillary track.

Most preferably the power source is one that is activated by application, to the device, of the liquid to be analyzed. It is particularly preferred that the sampling region is associated with electrodes of dissimilar metals which are such that when the liquid is applied to the device a current is generated. Metal arrays of Zinc and Silver:Silver chloride can generate voltages of 1.5 Volts and currents of 10 mAmps using a) saline solution and b) urine samples. At the present state of technology, the signal processing means could be an Integrated Circuit (IC) or an Application Specific Integrated Circuit (ASIC). ICs or ASICs driven at higher voltages can be manufactured at lower cost prices in the current market. The additional voltage can be achieved by presenting a number of electrodes of dissimilar metal in series, ensuring that each electrode pair in the series is separated by an aqueous impervious barrier.

Conveniently the electrodes of one of the metals alternate with the electrodes of the other (dissimilar) metal. Thus, for example, the electrodes may be in the form of 'combs' where of the teeth are inter-digitated. Conveniently such electrodes are provided beneath an absorbent pad at the sampling region.

Alternatively the power source may be a conventional battery (e.g. an alkaline battery) or a solar cell. In this embodiment, the interaction of the user in using the test would automatically activate the powering of the device. This may comprise pairs of electrodes, each such pair being within or underneath an absorbent pad so that wetting the pad with the application of the sample completes a circuit, powering the device. An alternative would be an action by the use, such as opening the test, or removing an external cap, physically removing a barrier to conductivity.

An exemplary embodiment of device in accordance with the invention has two parallel capillary channels (a "test capillary" and a "control capillary") of up to a length of 30 cm. These capillary channels may, in section, be in the form of an equilateral triangle with a side length of 50 to 100 μm. For this purpose, the device conveniently comprises an injection moulded base of, for example, polycarbonate or polystyrene, formed with V-shaped grooves which provide two sides of the capillary. A top plate of the same material as the base may subsequently be applied by, for example, ultrasonic welding to complete the capillary arrangement.

The exemplary device incorporates an upstream sample receiving chamber and a downstream detection arrangement of the type outlined above. The chamber may (but not necessarily) incorporate a pad which provides the advantage of minimizing spilling or splashing during sample testing. The pad may be of a fibrous material, e.g. cellulose, and a variety of materials are available commercially from suppliers such as Filtrona or Porex. Fibrous pads may exert a counter capillary force to the capillary channel and the selection of pad material will depend on the dimensions of the capillary channel since these determine the capillary force. A suitable pad material for the 500 μm triangular capillary channel is available from Filtrona under the code R22087.

Incorporated in the test capillary is an agglutination reagent system comprised of particles with immobilized antibody to hCG. In general, the larger the capillary channel the larger the diameter the particles need to be. A suitable particle size for the 500 micron triangular capillary is 5 microns. Examples of suitable particles include 5 μm polystyrene spheres from Polymer Laboratories.

The agglutination reagent system may be mixed with Sephadex G100 to produce a slurry comprised (w/v) 0.08-10% latex particles and 0.08-5% Sephadex. 1.6 μL of the mixture may be deposited over the first centimeter of the test capillary and dried by incubation at room temperature. This provides a plug which focuses the agglutination reaction and also provides a swelling material to help trap small agglutination complexes.

A similar slurry (but in which the latex beads do not incorporate the antibody to hCG) may be laid down and dried in the control capillary.

The device as described is suitable for detection of hCG in urine at concentrations indicative of pregnancy on the first day of the missed period (25 inIU/ml).

An additional factor for amplifying the effect of agglutination complexes on the flow rate is to incorporate weirs into the capillary channels. These function by reducing the surface tension (and therefore capillary draw) across the reduction in the capillary dimension, allowing agglutination complexes to precipitate out of solution and build up against the weir wall. A weir of 100 µm in a 500 µm triangular capillary is appropriate.

BRIEF DESCRIPTION OF THE DRAWINGS

The invention will be further described, by way of example only, with reference to the accompanying drawings, in which.

DETAILED DESCRIPTION

Figure 1:
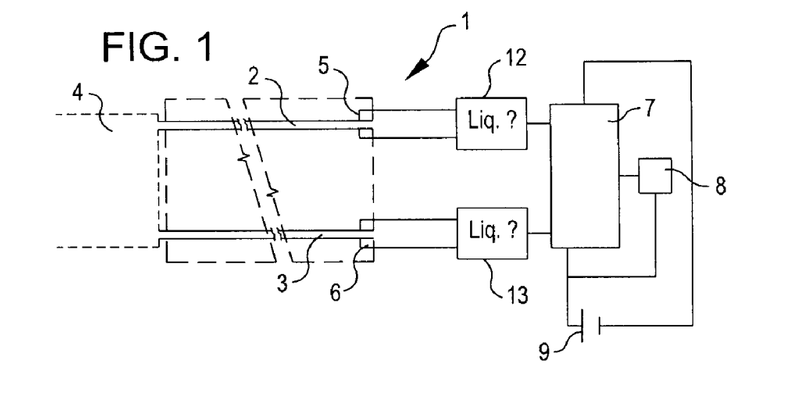
FIG. 1 schematically illustrates an embodiment of pregnancy testing device in accordance with the invention.

FIG. 1 schematically illustrates the principle of operation of a pregnancy testing device 1 for determining the presence or otherwise of hCG (human Chorionic Gonadotropin) in urine. The illustrated device 1 has two capillary pathways 2 and 3 associated at their upstream ends with an absorbent pad 4 and at their downstream ends with pairs of detection electrodes 5 and 6 respectively. Additional features of the illustrated device 1 are a logic circuit (chip) 7 which controls a display device (e.g. LCD device) 8, both the chip 7 and LCD device being associated with a power source 9. Each pair of electrodes 5 and 6 is associated with the chip 7 for the purpose to be described.

Capillary pathway 2 is referred to as the 'control track' and capillary pathway 3 as the 'test track'.

Provided in test track 3 as already mentioned in detail above is an agglutination reagent system comprised of latex beads 10 (see FIG. 2), e.g. having a diameter of 3-5 µm, on which anti-hCG antibody is immobilised. Additionally provided in the test track 3 downstream of the beads 10 is anti-hCG antibody immobilised on the inner walls of the test track 3. There is no agglutination reagent system in control track 2. An additional feature of the test track 3 is a weir 11, the purpose of which again will be described later.

As described above, each pair of electrodes 5 and 6 is associated with the logic circuit 7. The pairs of electrodes 5 and 6 serve, in effect, to detect the presence or otherwise (as represented by boxes 12 and 13) of liquid towards the downstream end of the capillary pathway 2 or 3 as appropriate. More particularly, a potential difference is applied across each of the electrode pairs 5 and 6. The presence of urine between the electrodes of electrode pair 5 will mean that a current can pass between the electrodes 5 and be detected by the logic circuit 7. Similarly the logic circuit 7 is able to detect the presence of liquid (urine) at the downstream end of capillary pathway 3.

The illustrated power source 9 may be a 'permanent source' e.g. a battery. Alternatively it may be a solar cell which generated power only when the device is removed from, say, a light opaque housing. A further possibility, which is preferred in accordance with the invention, is that the power source 9 comprises dissimilar metals arranged to generate a current by virtue of the presence of urine on the pad 4. However whatever the nature of the power source 9, the operation of the illustrated device 1 is the same.

More particularly, to perform a pregnancy test, the pad 4 is initially wetted with urine. As a result, urine is able to flow along both the control track 2 and test track 3.

Given that the device is working normally then urine will flow along control track 2 so as to reach the electrode pair 5. The presence of the urine between the electrodes 5 is detected by the logic circuit 7. This confirms that the device is working normally. If for any reason liquid does not reach the electrode pair 5 then this is an indication that the device is not functioning properly and an appropriate warning may be displayed on the LCD device.

Figure 2:
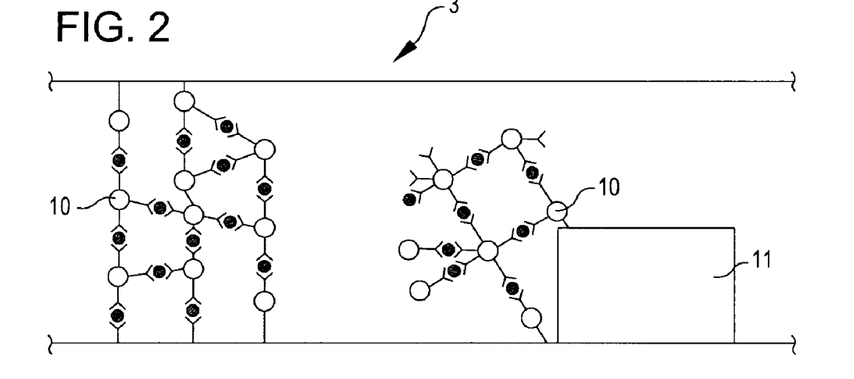
FIG. 2 illustrates to a much enlarged scale a portion of the testing pathway of the device in FIG. 1.

A urine sample from a pregnant woman will contain hCG represented in FIG. 2 by the solid black dot referenced as 13. This will bind both to the antibodies on the wall of the pathway 3 and to the antibodies on the latex beads 10. Additionally beads will agglomerate together by virtue of the hCG binding to antibodies on different beads. Alternatively the hCG may cause the beads to become immobilised on the inner wall of test track 3 (see FIG. 2).

It will thus be appreciated that, with urine from a pregnant woman, the beads 10 become immobilised on the inner walls of the test track 3 and/or agglomerate together. Agglomerates of beads may travel along the test track 3 but eventually meet the weir 11 which provides a constriction across the track. Agglomerates of beads will be held in this constrictions and, in effect, act as a dam to prevent or at least hinder urine originally taken into the upstream end of test track 3 reaching the electrode pair 6.

It will of course be appreciated that if the urine sample is from a woman who is not pregnant then the above described agglomeration of the beads does not occur so that the urine is able to reach the electrode pair 6.

The logic circuit 7 detects whether liquid has reached one, other or both of electrode pairs 5 and 6 and provides a display on the LCD device in association with the 'pattern' of liquid detected (or not detected) at the electrode pairs 5 and 6. The possibilities for all such 'patterns' are summarized in the following table where 'YES' indicates that liquid has been detected and 'NO' indicates that liquid has not been detected.

| ELECTRODE PAIR 5 | YES | YES | NO | NO |
|---|---|---|---|---|
| ELECTRODE PAIR 6 | YES | NO | NO | YES |
| RESULT | NOT PREGNANT | PREGNANT | DEVICE MALFUNCTION | DEVICE MALFUNCTION |

It will be appreciated that an appropriate message is then displayed on the LCD device 8.

Figure 3:
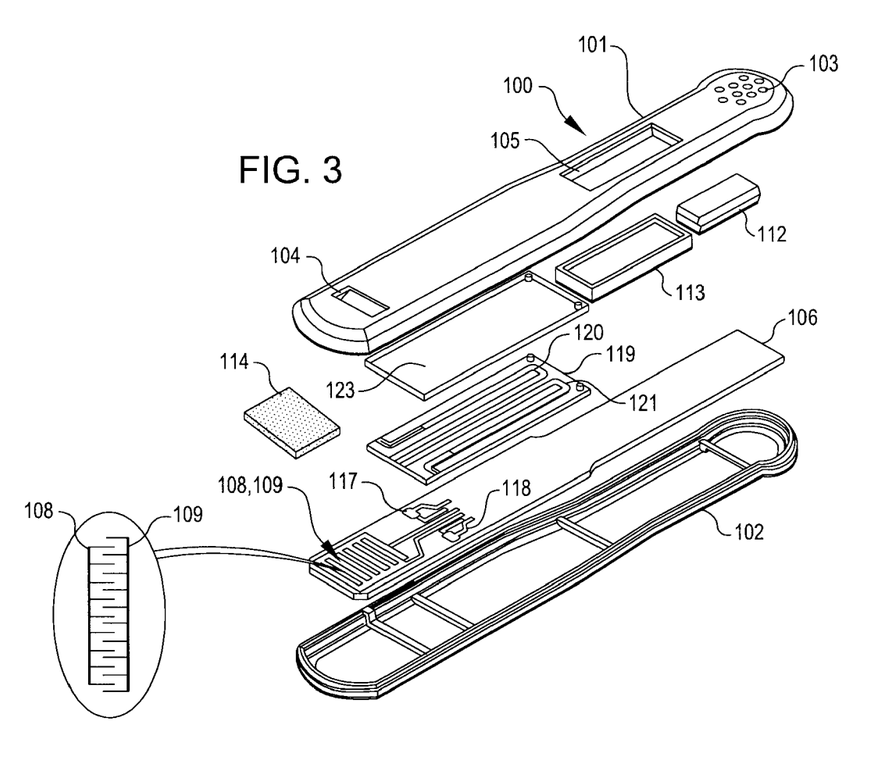
FIG. 3 is an exploded perspective view of a particular construction of device in accordance with the invention.

Reference is now made to FIG. 3 which illustrates a practical embodiment of pregnancy testing device 100 in accordance with the invention.

The device 100 comprises upper and lower elongate casing components 101 and 102 respectively which, in the assembled device, are securely clipped or sealed together.

In use, the device 100 is held at its right hand end (as viewed in FIG. 3) at which the casing components are provided with dimples affording 103 finger-grip formations. At the end of the device remote from the dimples 103, the upper casing component 101 is provided with an elongate aperture 104 (extending transversely to the length of the upper casing component 101) providing a sampling window. Intermediate the aperture 104 and the dimples 103 but nearer the latter is a further rectangular aperture 105, the purpose of which will be described below.

Within the assembled device 100 is a strip of Printed Circuit Board (PCB) 106 which extends along almost the entire length of the device. At its end below the aperture 104, the PCB 106 is printed with two 'combs' 108 and 109 of dissimilar metals. The teeth of one comb 108 are inter-digitated with the teeth of the other comb 109. In other words the teeth of comb 108 alternate with those of comb 109 (see appropriate view). The combs 108 and 109 together provide a power electrode array.

Electrical tracks 110 and 111 (not shown in full) connect the combs 108 and 109 to a logic circuit 112 and also to the LCD device 113 which (in the assembled device) is visible through aperture 105.

Although not shown in the drawing, there may be an arrangement of combs 108 and 109 on each side of the PCB 106, the two arrangements being multiplexed together.

An absorbent pad 114 is provided and (in the assembled device) sits on the combs 108 and 109 with its upper face being partially exposed in the aperture 104.

Also formed in the PCB 106 are two electrically conducting tracks 117 but not directly connected together. These tracks in effect correspond with one of the electrode pairs 5 and 6 described above with reference to FIG. 1 and are connected at their other ends to the logic circuit 112. Similarly a pair of tracks 118 extends, at one of their ends but are not directly connected at these ends and run at their other ends to the logic circuit 112. The electrode pairs 5 and 6 are positioned on the PCB such that they sit directly underneath holes in the capillary pathways 120 and 121. Each of these electrode pairs 117 and 118 may be covered with an absorbent fibrous material to facilitate transfer of liquid from 120 and 121 to 117 and 118.

Further provided within the device is a generally rectangular plate 119 formed on its upper surface with two channels 120 and 121. The plate locates within the device (by means of studs) such that one of its width wise edges abuts against the absorbent pad 114. Each channel 120 and 121 extends from (and opens out at) the width wise edge of the plate 119 abutting the pad towards the opposite end of the plate before turning back through 180° and subsequently turning through 90° to open out at a longitudinal edge of the plate.

Apertures (not shown) are provided in the 'floor' of each channel 120 and 121 where it turns through 90° to reach the longitudinal edge of the plate. With the plate located in position in the PCB board the aforementioned apertures locate one above each of the electrode pairs 117 and 118.

The plate 119 is associated with a lid 123 which cooperates with the plate to form capillary pathways from the channels 120 and 121.

One of the pathways is a control pathway and thus corresponds, in principle, exactly with the control track 2 described above with reference to FIG. 1. The other capillary pathway is a test track and therefore corresponds in principle with test track 3 described above with reference to FIG. 1. Each lane may incorporate two weirs positioned equidistant from each other and from the ends of the respective lane.

In use of the device 100, urine to be tested is applied to the absorbent pad via the aperture 104. As the pad wets, the urine comes into contact with the interdigitated combs 108 and 109 so that a current is generated. This current serves to operate the logic circuit 112 and, in effect, switches the device 'on'. Additionally, liquid from the pad enters the upstream ends of the two capillary pathways. Given that the device is working properly then urine passes along the control pathway 120 until it reaches the aperture in the track, at which point at least a portion of the urine from the control pathway 'drops' onto the PCB. The presence of urine on the PCB is detected by the logic circuit in view of the fact that a current can now pass between the electrode pair at 117. As previously mentioned an absorbent material placed over the electrodes at 117 will facilitate liquid transfer.

If the sample being analyzed contains the analyte (or contains the analyte in an amount above a predetermined value) then agglutination will occur in accordance with the principles described more fully above. As such, the liquid sample does not reach the aperture in track 121 so no current passes between the electrodes 118. As a result, the test is determined as negative. Conversely if the analyte is not present (or is present below a predetermined value) then liquid will pass fully along pathway 121 and 'drop' onto the PCB at 118 where it is detected.

In a modification of the above described embodiment, the absorbent pad 114 may be replaced by an enclosed liquid-holding reservoir associated with a one-way valve in the upper casing. Liquid sample to be analyzed may be passed through the one way valve into the reservoir from which it then passes into the capillary tracks.

We claim:

1. A method for testing for the presence of a component of interest in a liquid sample, comprising:
   (a) providing a sample testing device, wherein the device comprises:
      (i) at least one test capillary which has an upstream end and a downstream end and which incorporates an agglutination reagent system capable of causing agglutination with the component of interest;
      (ii) a sampling region for receiving the liquid sample and from which the liquid sample enters the upstream end of the test capillary;
      (iii) a power source;
      (iv) a detector electrically associated with the power source for detecting presence or absence of the liquid sample at the downstream end of the test capillary;
      (v) a display device operated by the power source for indicating a result of a test; and
      (vi) a signal processor associated with the power source, detector and display device for evaluating the result of the test and providing the result on the display device;
   (b) applying the liquid sample to the sampling region, whereby the liquid sample flows along the test capillary and contacts the agglutination reagent system and wherein the presence of the component of interest in the liquid sample causes agglutination that slows flow of the liquid sample such that the liquid sample does not reach the downstream end of the test capillary by a predetermined time, interval; and
   (c) detecting the presence or absence of the liquid sample at the downstream end of the test control capillary at the pre-determined time interval, wherein absence of the liquid sample at the downstream end of the test capillary at the pre-determined time interval is indicative of the presence of the component.

2. The method of claim 1, wherein measurement of the pre-determined time interval commences upon application of the liquid sample to the sampling region.

3. The method of claim 1, wherein the signal processor comprises a timer for measuring the pre-determined time interval.

4. The method of claim 1, wherein the sample testing device further comprises at least one control capillary having an upstream end and a downstream end, wherein the liquid sample enters the upstream end of the control capillary from the sampling region, and wherein the method further comprises detecting the presence or absence of the liquid sample at the downstream end of the control capillary at the pre-determined time interval.

5. The method of claim 4, wherein the presence of the liquid sample at the downstream end of the control capillary at the pre-determined time interval confirms that the sample testing device is functioning normally.

6. The method of claim 4, wherein the control capillary comprises a non-agglutinating reagent system.

7. The method of claim 1, wherein the power source comprises electrodes of dissimilar metals provided at the sampling region of the sample test device, the electrodes being adapted to generate a current when the liquid sample is applied to the sampling region.

8. The method of claim 7, wherein the electrodes of the dissimilar metals alternate with each other.

9. The method of claim 1, wherein the agglutination reagent system comprises beads on which is immobilized a binding partner for the component of interest.

10. The method of claim 9, wherein the binding partner is an antibody.

11. The method of claim 1, wherein the agglutination reagent system comprises a binding partner for the component of interest immobilized on walls of the test capillary.

12. The method of claim 11, wherein the binding partner is an antibody.

13. The method of claim 1, wherein the component of interest is human Chorionic Gonadotropin (hCG).

14. The method of claim 1, wherein the test capillary is formed by a co-operating plate and lid arrangement, the plate being formed with channels which become capillary tubes on location of the lid.

15. The method of claim 1, wherein the downstream end of the test capillary has at least one aperture and the detector is provided beneath the aperture.

16. The method of claim 1, wherein the detector comprises a pair of electrodes across which a potential difference is applied.

17. The method of claim 1, wherein the test capillary includes a particulate material to enhance a change in flow rate.

18. The method of claim 17, wherein the particulate material is an inert material.

19. The method of claim 18, wherein the inert particulate material is silica or bentonite.

20. The method of claim 17, wherein said particulate material is a swellable polymer.

* * * * *